United States Patent [19]

Buhler

[11] 4,243,304
[45] Jan. 6, 1981

[54] CONVERGENCE MECHANISM FOR BINOCULAR REFRACTING INSTRUMENT

[75] Inventor: Rato R. Buhler, Dudley, Mass.

[73] Assignee: American Optical Corporation, Southbridge, Mass.

[21] Appl. No.: 16,456

[22] Filed: Feb. 28, 1979

[51] Int. Cl.³ .......................... A61B 3/02; A61B 3/10
[52] U.S. Cl. ........................................ 351/27; 351/26; 351/5
[58] Field of Search ...................... 351/26, 27, 28, 29, 351/5

[56] References Cited

U.S. PATENT DOCUMENTS 2,293,200  2/1960  Wright .................................. 351/29
3,413,056  11/1968  Ishihara ................................ 351/28

Primary Examiner—John K. Corbin
Assistant Examiner—Rodney B. Bovernick
Attorney, Agent, or Firm—Jeremiah J. Duggan; Alan H. Spencer

[57] ABSTRACT

A mechanism which has a continuously variable amount of convergence and inward movement over the entire range of pupillary distance (PD) settings is disclosed. The repositioning of a pair of straight tracks transfers a continuously variable amount of motion to a pair of respective levers that control the position of a pair of carriages relative to the PD control and the angular relationship of lens batteries relative to the respective carriages.

5 Claims, 7 Drawing Figures

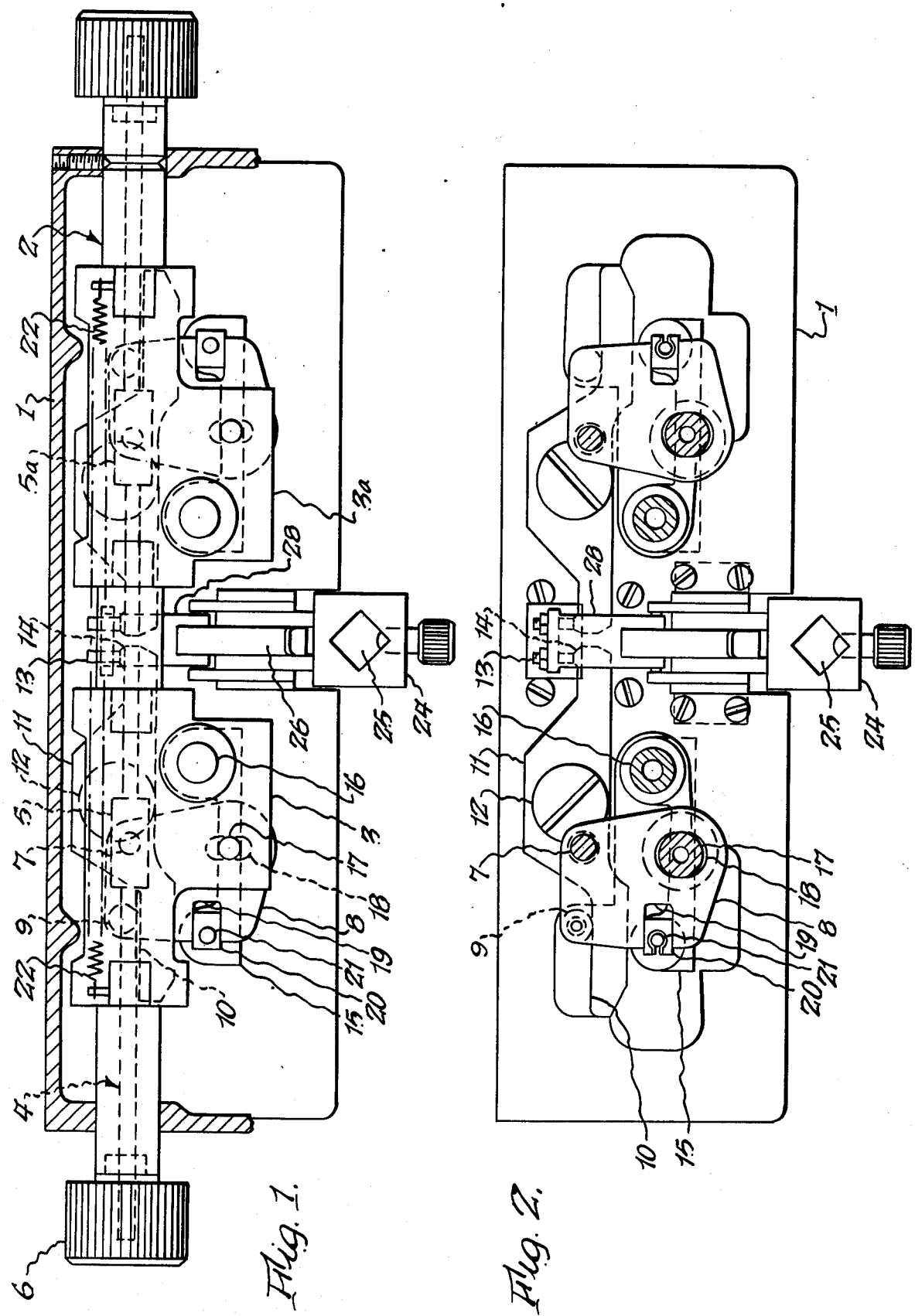

CONVERGENCE MECHANISM FOR BINOCULAR REFRACTING INSTRUMENT

BACKGROUND OF THE INVENTION

This invention relates to a binocular refractor and, more particularly, to a binocular refractor having an infinitely variable convergence mechanism over the entire range of PD settings from narrow to wide for proper alignment of test lenses on the vision axes of a patient's eyes for both near and distant testing.

PRIOR ART

U.S. Pat. No. 2,923,200 issued Feb. 2, 1960 describes a convergence mechanism for a binocular refractor. Each battery is connected to a cam and when the respective cam is actuated, the battery rotates a fixed amount and slides toward the other battery. Instruments of this type normally have the amount of rotation and inward movement selected to accomodate the majority of patients refracted. However, there is no charge in the amount of rotation or inward movement in such instruments permitting precise alignment of the test lenses with the visual axes during near testing for patients having either a greater or lesser PD than the "normal" PD.

U.S. Pat. No. 3,413,056 issued Nov. 26, 1968 describes a modification of the '200 mechanism for rotating a lens battery and moving the same toward the other lens battery when a single control is actuated.

BRIEF DESCRIPTION OF THE PRESENT INVENTION AND DRAWINGS

The present invention utilizes three tracks. One track supports a carriage for each respective lens battery to align one or more of a plurality of lenses with a patient's eyes. The other two tracks are movable from a normal position. When located in the normal position, these tracks are parallel to the first track. Contacts that follow the other tracks control the angular position of the respective lens batteries as well as their spacing relative to the PD adjustment. A single control moves the other tracks from their normal position to an alternate position that is both displaced from the normal position and at an angle thereto. Because of the angular relationship, the contacts travel different distances when they are located at different positions along the tracks as the tracks change from the normal to the alternate position. The variation in contact travel is used to vary the amount of convergence and inward movement of the lens batteries thereby maintaining alignment of the visual axes of the patient with the respective lens optical axis irrespective of the patient's PD.

FIG. 1 is a top view of the PD control and convergence mechanism,

FIG. 2 is a top view of the convergence mechanism assembly,

Figure 3:
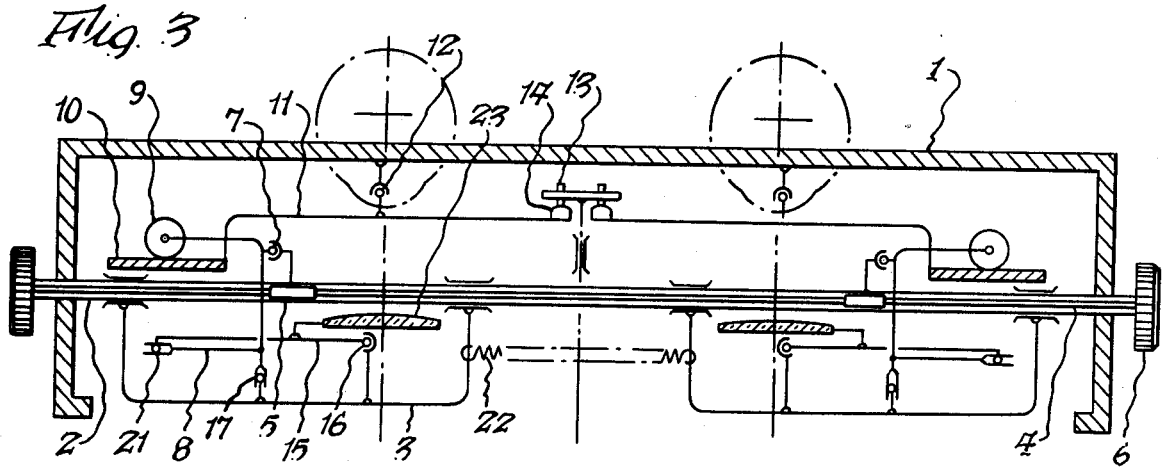
Figure 4:
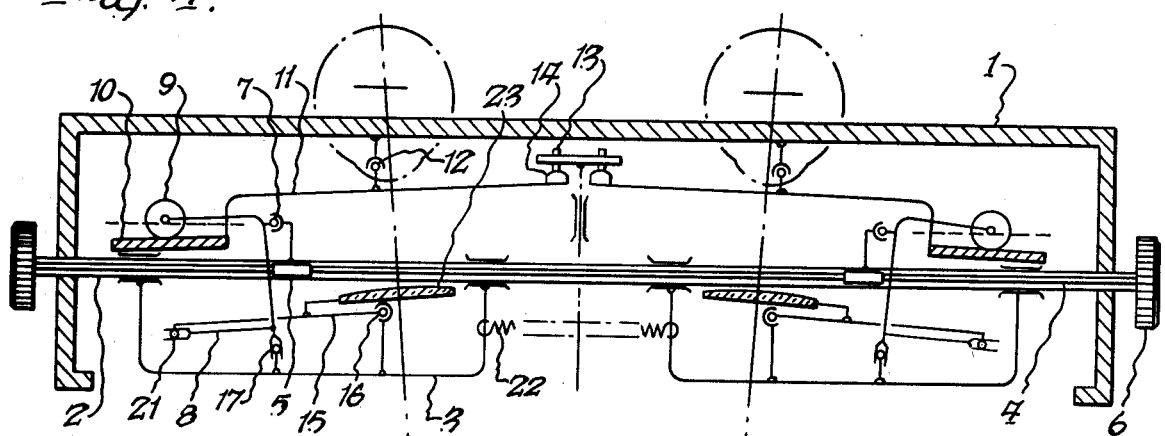
Figure 5:
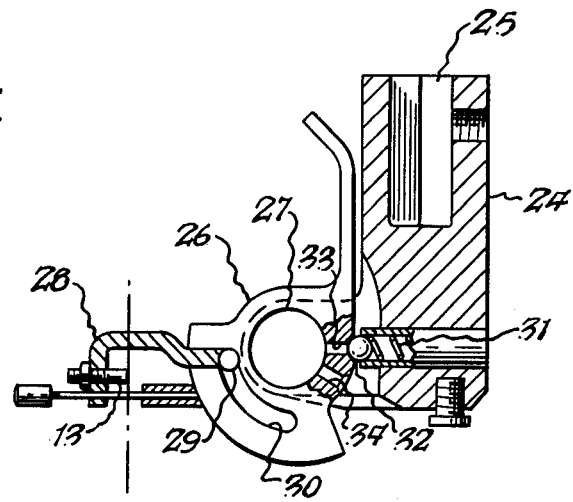
Figure 6:
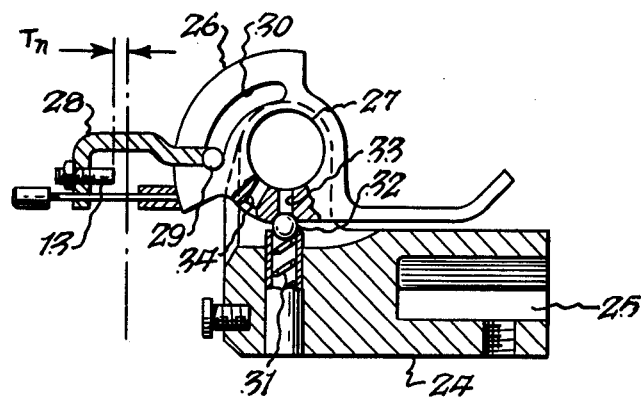
Figure 7:
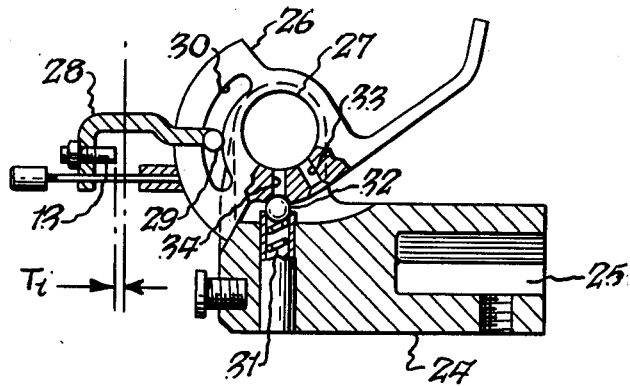

FIG. 3 is a mechanical diagram of the PD control and convergence mechanism positioned for distant testing, FIG. 4 is a mechanical diagram of the PD control and convergence mechanism positioned for near testing, FIG. 5 is a side view of the convergence actuating mechanism positioned for distant testing, FIG. 6 is a side view of the convergence actuating mechanism positioned for near testing, and FIG. 7 is a side view of the convergence actuating mechanism positioned for intermediate testing.

DETAILED DESCRIPTION OF THE PREFERRED EMBODIMENT

Referring to FIG. 1, frame 1 supports a pair of lens batteries, for presenting one or more of a plurality of test lenses along the visual axis of a patient's eyes, and has track 2 extending therethrough. A pair of carriages 3 and 3a are carried by track 2. Shaft 4 threadably engages nut 5 and nut 5a. Nuts 5 and 5a have reverse threads, i.e. one has left-hand threads and one has right-hand threads, in order to move carriages 3 and 3a toward each other when knob 6 is turned in one direction and away from each other when knob 6 is turned in the other direction in order to adjust the spacing between the test lens to accomodate the PD of diverse individuals. Since the right-hand mechanism is a mirror image of the left-hand mechanism, only those elements on the left-hand side will be specifically identified hereinafter. Pin 7 extends up from nut 5. Also, by referring to FIG. 2, it can be seen that lever 8 is pivotably mounted to pin 7. Roller 9 is carried by lever 8 and engages surface 10 of arm 11. Arm 11 is pivotably mounted to frame 1 by pivot screw 12 and is positioned by set screw 13 bearing against face 14 of arm 11.

Battery support 15 is pivotably connected to carriage 3 by pivot 16. Shoulder screw 17, extending from battery support 15, and slot 18 in lever 8, combine to transfer sliding motion through lever 8 from nut 5 to carriage 3. Pivotable motion is transferred from lever 8 through recess 19, block 20 and pin 21 to battery support 15. Spring 22 urges carriages 3 and 3a toward a central position of convergence.

The operation of the infinitely variable convergence mechanism will be described by reference to FIGS. 3 and 4. Pressure from spring 22 on carriage 3 is transmitted through shoulder screw 17 and lever 8 to force roller 9 against surface 10, which acts as a track for roller 9. Pivotal motion of arm 11 is resisted by pressure of set screw 13 against face 14. In FIG. 3, representative test lens 23 is located on the visual axis of a patient's eye aligned to view an object at an infinite distance, usually twenty feet. To converge the lens batteries for viewing at a near distance, set screw 13 is moved from the position shown in FIG. 3 to the position shown in FIG. 4 by structure to be described hereinafter. Since the bias force transferred from spring 22 forces face 14 to follow set screw 13, arm 11 is pivoted about pivot screw 12 causing surface 10 to move toward and assume an angular relationship with respect to track 2. As roller 9 follows surface 10, lever 8 pivots about pin 7 allowing carriage 3 to slide inward along track 2 toward the center of frame 1. Simultaneously, battery support 15 is rotated about pivot 16 by movement of lever 8 transmitted to battery support through pin 21.

Returning to FIG. 3, it can be easily seen that if the pupillary distance is adjusted by rotation of knob 6 the parallel relationship between surface 10 and track 2 prevents pivotal movement at pin 7 as roller 9 tracks along surface 10. Therefore, test lens 23 is maintained in a position for viewing at an infinite distance and carriage 3 moves the same distance as nut 5.

The dotted line in FIG. 4 shows surface 10 in the position illustrated in FIG. 3. The continuously changing space between the dotted line and surface 10 shows that the amount of movement transferred through roller 9 to lever 8 is continuously varied as the location of roller 9 along surface 10 is changed. A patient having a narrow PD would cause a relocation of roller 9 to a position to the right of that illustrated in FIG. 4. This relocation would result in a smaller amount of sliding motion in carriage 3 and a lesser amount of rotation of lens 23 as set screw 13 moves from the position shown in FIG. 3 to the position shown in FIG. 4, since roller 9 moves a shorter distance in following surface 10. Conversely, a patient having a large PD would result in a relocation of roller 9 to the left of the position shown in FIG. 4 which would result in a greater amount of inward movement of carriage 3 and greater amount of rotation of test lens 23 as a result of the larger movement of roller 9 while following surface 10 as it moves from the dotted position to the position shown in FIG. 4.

Referring to FIG. 1, rod holder 24 is pivotably mounted on frame 1. Socket 25 is adapted to receive a rod (not shown) for supporting the near point reading chart. Referring now to FIG. 5, rod holder 24 and cam 26 are both pivotally mounted to frame 1 by sleeve 27. Sliding member 28 positions set screw 13 in alignment with face 14 and the other end of member 28 carries cam follower 29 which rides in recess 30 of cam 26. Spring 31 urges ball 32 into near detent 33 or alternatively intermediate detent 34 as shown in FIGS. 6 and 7 respectively. For near point examination, maximum convergence and inward movement of the batteries is provided by the movement of set screw 13 over the distance Tn as shown in FIG. 6 when both rod holder 24 and cam 26 are rotated the full distance.

FIG. 7 illustrates the location of ball 32 in detent 34 when rod holder 24 is rotated the full distance but cam 26 is only partially rotated. As shown in FIG. 7, intermediate distance Ti is less than the distance travelled by set screw 13 shown in FIG. 6. since set screw 13 moves a smaller distance when cam 26 is in the intermediate position, a correspondingly smaller movement of surface 10 is permitted. Therefore, the amount of inward movement and rotation is less in each of the lens batteries when the instrument is set for an intermediate distance.

What is claimed is:

1. A mechanism for converging a pair of lens batteries used for binocular refraction of patient's eyes at near and far distances which comprises, a frame, a straight fixed track supported by said frame, a shaft rotatably supported by said frame, and shaft having a left-hand threaded portion and a right-hand threaded portion and extending parallel to said track, a pair of nuts threadably engaging a respective portion of said shaft, a pair of straight, selectively movable tracks mounted on said frame, each of said pair of straight movable tracks having a normal position and an alternate position, said normal position being parallel to said fixed track, said alternate position being spaced from and at a chosen angle to said normal position, a pair of carriages slidably mounted on said fixed track, a carriage connecting lever pivotably mounted on each of said pair of nuts, contact means extending from each lever and engaging a respective one of said movable tracks for rotating each lever when said movable tracks change from one of said positions to the other, support means pivotably mounted on each of said carriages for supporting a respective one of the lens batteries, connection means for transferring pivotal motion of each lever to said support means in each case, and positioning means for selectively moving said pair of movable tracks from said normal position to said alternate position.

2. The mechanism of claim 1 wherein said movable tracks are pivotably mounted to said frame.

3. The mechanism of claim 1 wherin said contact means includes a roller rotatably mounted on each lever.

4. The mechanism of claim 1 wherein each lever has a pair of elongated slots, said slots extending in perpendicular directions, one of said slots being a part of said conection means and cooperating with a member extending from the respective support means and the other of said slots cooperating with a member extending from the respective carriage.

5. In a refractor having a pair of lens batteries for binocular refraction of a patient's eyes, a frame, a straight fixed track mounted to said frame, a pair of carriages for carrying said lens batteries and being slidable along the fixed track, adjustment means for varying the spacing between the carriages, and common actuating means for converging the lens batteries, each lens battery having an improved convergence mechanism comprising, a pivot driven by the adjustment means along a path parallel to said fixed track, a lever pivotably mounted on said pivot, said lever having a normal position, a first elongated slot in said lever, said first elongated slot extending in a direction perpendicular to the fixed track when said lever is in the normal position, a member protruding from the respective carriage and engaging said first elongated slot, a second elongated slot in said lever, said second elongated slot extending in a direction parallel to the fixed track when said lever is in the normal position, a lens battery support member pivotably connected at one end to the respective carriage, a protrusion extending from the other end of said support member into said second elongated slot, an arm having a proximate end, a distal end, and a normal position, pivot means intermediate said ends for mounting said arm on the frame, a straight surface at said proximate end, said surface being aligned parallel to the fixed track when said arm is in its normal position, said distal end being in engagement with the common actuating means, a roller mounted to said lever proximate to said surface and biasing means urging said roller in engagement with said surface.

* * * * *